(12) United States Patent
Hermonat et al.

(10) Patent No.: US 6,495,361 B1
(45) Date of Patent: Dec. 17, 2002

(54) METHOD OF PRODUCING INFECTIOUS PAPILLOMAVIRUS IN PLACENTAL CELLS

(75) Inventors: Paul L. Hermonat; Yong Liu, both of Little Rock, AR (US)

(73) Assignee: University of Arkansas, Little Rock, AR (US)

( * ) Notice: Subject to any disclaimer, the term of this patent is extended or adjusted under 35 U.S.C. 154(b) by 0 days.

(21) Appl. No.: 09/621,579

(22) Filed: Jul. 21, 2000

(51) Int. Cl.$^7$ ................................................ C12N 7/00
(52) U.S. Cl. ............................ 435/235.1; 435/5; 435/4; 435/7.1; 435/236; 435/239; 435/173.6
(58) Field of Search ................................ 435/235.1, 7.1, 435/4, 5, 236, 239, 173.6

(56) References Cited

U.S. PATENT DOCUMENTS 5,994,115 A    11/1999    Meyers .................... 435/235.1

OTHER PUBLICATIONS

M.G. Frattini et al., "In vitro synthesis of oncogenic human Papillomaviruses Requires Episomal Genomes For differentiation–dependent late expression", *Proc. Nat. Acad. Sci.*, vol. 93, pp. 3062–3067, (1996).

P.L. Hermonat et al., "Human Papillomavirus is More Prevalent in First Trimester Spontaneously Aborted Products Of Compared to Elective Specimens", *Virus Genes*, Kluwer Academic Press, vol. 14:1, pp. 13–17, (1997).

P.L. Hermonat et al., "Trophoblasts are the Preferential Target for Human Papilloma Virus Infection In Spontaneously Aborted Products of Conception", Human Pathology, W.B. Saunders Company, vol. 29:2, pp. 170–174, (1998).

M.Melbye et al., "The role of human papillomaviruses in anogenital cancers", *Cancer Biology, The Academic Press*, vol. 8, pp. 307–313, (1998).

C. Meyers, "Organotypic (raft) epithelial tissue culture system For The Differentiation–Dependent replication of papillomavirus", Methods in Cell Science, vol. 18, pp. 201–210, Sep. 1996, Kluwer Academic Publishers.

C. Meyers et al., "Biosynthesis of Human Papillomavirus from a Continuous Cell Line Upon Epithelial Differentiation", *Science*, vol. 257, pp. 971–973, (1992).

C. Meyers et al., "Synthesis of Infectious Human Papillomavirus Type 18 in Defferentiating Epithelium Transfected With Viral DNA", *J. Virology*, vol. 71:10, pp. 7381–7386, Oct. 1997, American Society for Microbiology.

C. Meyers et al., "Tissue Culture Techniques for the Study of Human Papilloma Viruses in Stratified Epithelia", *Cell Biology*, vol. 1, Second Edition, pp. 513–520, (1998), Academic Press.

C. C. Pao et al., "Human Papillomavirus Type 18 DNA in Gestational Trophoblastic Tissues And Choriocarinomas", *Int. J. Cancer*, Wiley–Liss, Inc., vol. 63, pp. 505–509, (1995).

Genest, D. R. et al., "Human papillomavirus in spontaneous abortion," *Human Pathology*, 30(1):109–110 (Jan. 1999) ISSN: 0046–8177 XP 008006630.

Krouse R. S. et al., "rAAV Vector Transducation of Dendritic Cells (DC) for Development of Tumor Specific Vaccines," *Blood*, W. B. Saunder, Philadelphia, VA 92(10) Suppl. 1/2:146A–147A (Nov. 15, 1998) ISSN: 0006–4971 XP 000978926.

Alani R. M. et al. "Human Papillomaviruses and Associates Malignancies," *Journal of Clinical Oncology*, 16(1): 330–337 (Jan. 1998) ©American Society of Clinical Oncology ISSN: 0732–183x XP008006664.

Vinatier, D. et al., "Prophylactic and therapeutic vaccinotherapies in *Papillomavirus* infections," *Gyneol Obstet Fertil* 28(5):370–384 (2000) ©Editions scientifiques et medicales Elsevier SAS ISSN: 1297–9589 XP0080066665.

Liu, Y. et al., "Display of Complete Life Cycle of Human Papillomavirus Type 16 in Cultured Placental Trophoblasts," *Virology* 290:99–105 (2001) ©Academic Press ISSN: 0042–6822 XP002198252.

*Primary Examiner*—Ali R. Salimi
(74) *Attorney, Agent, or Firm*—Foley & Lardner

(57) ABSTRACT

The present invention is discloses an improved method of producing infectious papillomavirus in vitro, with a method comprising (a) introducing papillomavirus or papillomavirus DNA or portions thereof necessary for replication, into an epithelial cell; and (b) providing conditions that produce papillomavirus, wherein the conditions comprise not contacting the epithelial cell a fibroblast and does not comprise an organotypic raft culture or a dermal equivalent. The present invention also discloses a papillomavirus infected non-keratinocyte epithelial cell produced by the methods of the present invention. Further, uses of the disclosed method includes detection methods, methods for screening anti-papillomavirus drugs, methods of making recombinant papillomavirus for vaccines and studying the life cycle. Additionally, a method of reducing and assessing the risk of spontaneous abortion is disclosed.

7 Claims, 5 Drawing Sheets

METHOD OF PRODUCING INFECTIOUS PAPILLOMAVIRUS IN PLACENTAL CELLS

BACKGROUND OF THE INVENTION

The present invention relates to an improved method of producing infectious papillomavirus in vitro, with a method comprising (a) introducing papillomavirus or papillomavirus DNA or portions thereof necessary for replication, into an epithelial cell; and (b) providing conditions that produce papillomavirus, wherein the conditions comprise not contacting the epithelial cell a fibroblast or an organotypic raft culture or dermal equivalent.

In earlier studies it was found that HPV infection is threefold more prevalent in spontaneous aborted products of conception compared to elective abortions (60% vs 20%), and that the HPVs were preferentially infecting the trophoblasts within the placenta (1,2). Other studies are supportive of our findings (3–5), that HPVs are present in spontaneous abortions or in trophoblasts. Malhomme et al. (1997)(3) have found that 70% of spontaneous abortion specimens contain HPV by PCR analysis. In addition, Sikstrom et al. (1995) found that women with a history of HPV infection had a higher risk of spontaneous abortion (odds ratio of 3) (6). Pao et al. (1995) found that HPV-18 was present in 50% of choriocarcinomas (malignant trophoblasts) and in some placentas (7). Also related to this issue, HPV DNA has been detected by PCR amplification of DNA from cells taken from amniotic fluids of pregnant women with evidence of HPV genital infection (60% HPV positive), indicating that HPV has the capacity to cross the placental barrier when already present in the cervix (8). In the same report the investigators were unable to detect HPV DNA sequences in amniotic fluid cells from women with no cervical HPV infection.

Trophoblasts are the cells of the placenta that are in direct contact with the maternal tissues. These cells are critical for anchoring the placenta to the maternal tissues. It is also through the trophoblasts that all nutrient exchange and waste exchange takes place. Thus, the disruption of the trophoblastic layer, by HPV or any other infectious or chemical agent, could likely result in abnormal plantation and subsequent expulsion of the gestation (5,9).

The present invention demonstrates that HPV-16 is fully active in trophoblasts. HPVs are already well known to be pathogenic viruses, and are the largest risk factor in the development of cervical cancer (18). Thus, trophoblasts become the second host cell type, in addition to the well studied replication of HPVs in differentiating keratinocytes. These data also support the hypothesis that HPV infection of trophoblasts may be linked to some spontaneous abortions. The search for factors that may be implicated in spontaneous abortion has led to the examination of numerous factors, including maternal age, environmental exposures, tobacco use, and nutritional factors (19–29). However, the studies exploring these relationships have been inconsistent in their findings. For every study supporting an association with spontaneous abortions, there is another study that does not support a relationship. The only uncontested factor thus far is maternal age. If the link between HPV infection and gestational loss can be further substantiated then specific treatment protocols might be developed. Finally, these data represent a technological advance in the ease of studying or generating HPVs, over the tedious and expensive organotypic raft culture system as described in (15) and in U.S. Pat. No. 5,994,115.

SUMMARY OF THE INVENTION

The present invention is directed to an improved method of producing infectious papillomavirus in vitro, with a method comprising (a) introducing papillomavirus or papillomavirus DNA or portions thereof necessary for replication, into an epithelial cell; and (b) providing conditions that produce papillomavirus, wherein the conditions comprise not contacting the epithelial cell a fibroblast.

Further, the present invention is directed to a method of producing infectious papillomavirus in vitro, comprises (a) introducing papillomavirus or papillomavirus DNA or portions thereof necessary for replication, into an epithelial cell; and (b) providing conditions that produce infectious papillomavirus, wherein the conditions comprise the epithelial cell not contacting an organotypic raft culture or a dermal equivalent.

Additionally, the present invention also is directed to a papillomavirus infected non-keratinocyte epithelial cell produced by the method comprising (a) introducing papillomavirus or papillomavirus DNA or portions thereof necessary for replication, into an epithelial cell; and (b) providing conditions that produce papillomavirus, wherein the conditions comprise not contacting the epithelial cell a fibroblast.

The present invention is further directed to a method of detecting the presence of papillomavirus in a subject comprising: (a) introducing papillomavirus or papillomavirus DNA or portions thereof necessary for replication, into an epithelial cell; (b) providing conditions that produce infectious papillomavirus in the epithelial cell, where the conditions comprise the epithelial cell not contacting a fibroblast; and (c) detecting the presence of papillomavirus in the epithelial cell.

The present invention further is directed to a method of evaluating the inhibition of a papillomavirus comprising (a) introducing papillomavirus or papillomavirus DNA or portions thereof necessary for replication, into an epithelial cell; (b) providing conditions that produce infectious papillomavirus in the epithelial cell, wherein the conditions comprise the epithelial cell not contacting a fibroblast; (c) contacting a potential inhibitor of papillomavirus with the infectious papillomavirus produced in the epithelial cells; and (d) evaluating the presence or absence of the papillomavirus to determine the effectiveness of potential inhibitors.

The present invention also is directed to a method of producing a mutant or recombinant papillomavirus, wherein the method comprises: (a) introducing mutant or recombinant papillomavirus DNA or portions thereof necessary for replication, into an epithelial cell; and (b) providing conditions that produce infectious mutant or recombinant papillomavirus in the epithelial cell, wherein the conditions comprise epithelial cell not contacting a fibroblast.

The present invention further is directed to a method of producing a non-keratinocyte epithelial helper cell for production of mutant or recombinant papillomavirus comprising: (a) introducing papillomavirus DNA or portions thereof, into a non-keratinocyte epithelial cell, wherein the DNA or portions thereof, supplements the replication of the mutant or recombinant papillomavirus; and (b) providing conditions that produce said non-keratinocyte epithelial helper cell containing said papillomavirus DNA or portions thereof, that supplements the replication of the mutant or recombinant papillomavirus, wherein the conditions comprise the epithelial cell not contacting a fibroblast.

A method of reducing the risk of spontaneous abortion caused by papillomavirus comprising administering to a subject at risk of spontaneous abortion a drug that inhibits papaillomavirus.

DETAILED DESCRIPTION OF THE PREFERRED EMBODIMENT

Figure 1A:
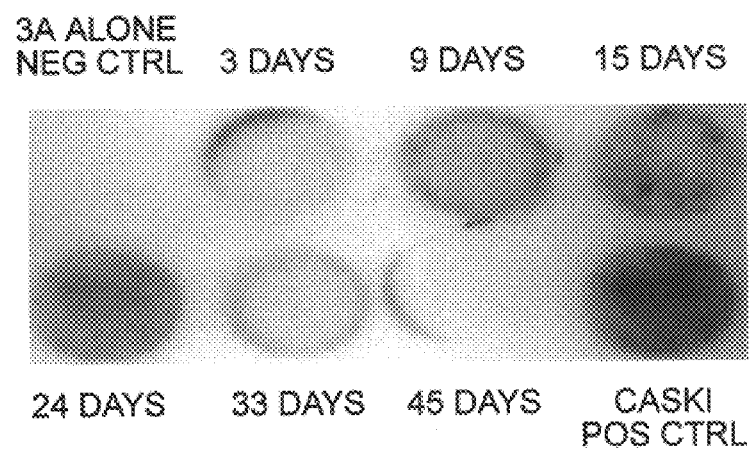
FIG. 1: HPV-16 DNA replication in 3A trophoblasts. A Analysis by infectious center assay. This study was carried out similar to that described previously (26). Note positive signals at days 9–24. B Analysis by Southern blot assay. Five $\times 10^5$ 3A cells were transfected with 1 $\mu$g recircularized HPV-16 genomic DNA and harvested at the indicated times. The total cellular DNA were digested by both of Dpn I and BamH I, agarose gel electrophoresed,Southern blotted, at probed with $^{32}$P-HPV-16 DNA. Note high positive signals at days 9–24. C Another analysis by Southern blot assay. Th experiment was similar to B, with harvesting at day 14 and digestion with the indicated restriction enzymes. Note that forms I, II, and III DNA are seen in the undigested lane and appropriate sized fragments are seen in the Eco RI, Nde I, and Pst I digested lanes.

The present invention is directed to an improved method of producing infectious papillomavirus in vitro in an epithelial cell without the need of an additional cell type to produce papillomavirus, and particularly infectious papillomavirus. The present invention requires only the use of a monolayer culture of epithelial cells, and as a result provides an advance over the prior art.

The present invention is directed to an improved method of producing infectious papillomavirus in vitro, with a method comprising (a) introducing papillomavirus or papillomavirus DNA or portions thereof necessary for replication, into an epithelial cell; and (b) providing conditions that produce papillomavirus, wherein the conditions comprise not contacting the epithelial cell with a fibroblast. The epithelial cell into which the virus or DNA is introduced in the method is not a keratinocyte or a keratinocyte cell line. Further, the present method of producing infectious papillomavirus in vitro, comprises (a) introducing papillomavirus or papillomavirus DNA or portions thereof necessary for replication, into an epithelial cell; and (b) providing conditions that produce infectious papillomavirus, wherein the conditions comprise the epithelial cell not contacting an organotypic raft culture or a dermal equivalent. The organotypic raft tissue culture system accurately mimics an in vivo cellular environment and architecture mimics a dermal equivalent and is described in detail in U.S. Pat. No. 5,994,115 as well as in (15). More specifically, the present method producing infectious papillomavirus in vitro, consisting essentially of the steps of (a) introducing papillomavirus or papillomavirus DNA or portions thereof necessary for replication, into an epithelial cell; and (b) providing conditions that produce infectious papillomavirus.

In a preferred embodiment, the epithelial cell in the above-described methods is not a keratinocyte as described in U.S. Pat. No. 5,994,115, and more preferably the epithelial cell is a placental cell or a placental cell line. In a more preferred embodiment, the placental cell is a trophoblast or types of trophoblasts, such as a cytotrophoblast, a syncytiotrohoblast, a displastic trophoblast or a choriocarcinoma. A trophoblast is defined as a layer of extraembryonic ectodermal tissue on the outside of the blastocyst and from it is derived the chorion and amnion. The inner cellular layer of the trophoblast covering a chorionic villus is called a cytotrophoblast and its outer syncytial layer is called a syncytiotrophoblast. A choriocarcinoma is a malignant trophoblast and a hyperplastic or displastic trophoblast is an abnormal trophoblast. Extraembryonic ectoderm is defined as a derivative of epiblast or ectoderm located outside the body of the embryo. (Dorland's Illustrated Medical Dictionary, $25^{th}$ Ed. W. B. Sanunders Comp., 1974, page 492 and 1648). Further, he trophoblast is defined as the outer, ectodermal epithelium of the mammalian blastocyst or chorion and chorionic villi. (Blakison's Pocket Medical Dictionary, $3^{rd}$ Ed., McGraw-Hill Book Comp., 1973, page 803). Therefore, the trophoblast is defined as an epitheilal cell, albeit, a specialized one.

Any of the above described trophoblasts are useful in the present invention to produce infectious papillomavirus, However, particularly, useful in the present method and used as a representative example in the experimental section of this disclosure, is a human placental cell transformed by SV40 and designated as 3A cells and particularly, 3A(tPA-30-1). This cell line is publicly available from the American Type Culture Collection , ATCC NO. CRL-1583 and also described in (10), a publication by the depositor of the 3A cells.

The method of producing a papillomavirus in vitro according to the present invention introduces a papillomavirus inoculum or papillomavirus DNA or portions thereof necessary for replication of papillomavirus into an epithelial cell, such as the trophoblast described above by any number of known methods. For example, the introduction of the papillomavirus DNA can be by transfection into the epithelial cell, which means the uptake and expression of DNA by a eukaryotic cell. Additionally, the DNA can be taken up by the epithelial cell by lipofection using a lipid. Additionally, electroporation can be used by applying electric pulses to animal cells to increase the permeability of the cell membranes to facilitate DNA uptake into the cell. The DNA that is introduced into the endothelial cells and trophoblasts of the present invention is preferably papillomavirus genomic DNA but portions of genomic DNA or cDNA or portions thereof also are intended by the present invention. Additionally, papillomavirus mutant DNA may be introduced into the epithelial cell so that when expressed in the epithelial cell, an attenuated or defective infectious papillomavirus is produced by the present method. Mutations can be introduced into the DNA to modify portions of known genes with know functions. Mutated DNAs can be fused to form chimeric DNAs that are expressed and produce papillomavirus with specific properties. Particularly, useful is the preparation of attenuated or defective papillomaviruses for use in making vaccines against papillomavirus. These attenuated viruses have been weakened by genetic manipulation, so that they stimulate the immune system but are unable to cause a papillomavirus infection. The viruses may still be capable of infection but limited in its pathogenicity. However, mutant papillomaviruses can be produced that are defective in DNA replication or oncogenic transformation but the mutant virus particle would still be able to infect target cells and introduce the mutant DNA into the cell, resulting in the expression of the mutant DNA with its appropriate defective phenotype.

Further, papillomavirus from a subject sample or virus stock may be directly contacted with the epithelial cell, thereby infecting the epithelial cell with the papillomavirus to obtain amplification or increasing papillomavirus numbers for use in the methods of the present invention.

The method of the present invention is useful to produce any type of papillomavirus, which is a subgroup of the papovaviruses. The human papillomavirus is preferably produced by the present invention but papillomavirus that causes paillomata and papilloma diseases in other species, such as rabbits, cows, dogs, pigs, and various other animals are also encompassed by the methods and cells of the present invention.

The present invention also is directed to a papillomavirus infected non-keratinocyte epithelial cell produced by the method comprising (a) introducing papillomavirus or papillomavirus DNA or portions thereof necessary for replication, into an epithelial cell; and (b) providing conditions that produce papillomavirus, wherein the conditions comprise not contacting the epithelial cell with a fibroblast. The epithelial cell is not a keratinocyte or a keratinocyte cell line. Further, the papillomavirus infected epithelial cell of the present method is produced in vitro with a method comprising (a) introducing papillomavirus or papillomavirus DNA or portions thereof necessary for replication, into an epithelial cell; and (b) providing conditions that produce infectious papillomavirus, wherein the conditions comprise the epithelial cell not contacting an organotypic raft culture or a dermal equivalent. The papillomavirus infected epithelial cell produced by these methods is preferably a placental cell. More preferably, the papillomavirus infected epithelial cell is a placental cell, more preferably selected from the group consisting of a trophoblast, a cytotrophoblast, a syncytiotrohoblast, a hyperplastic or displastic trophoblast and a choriocarcinoma. Preferably the papillomavirus infected epithelial cell is infected with a human papillomavirus. The papillomavirus infected target cells, such as trophoblasts, can be used to infect other cells, such as keratinocytes, if one wishes to study or compare this prior art system to the method of the present invention.

The present invention is further directed to a method of detecting the presence of papillomavirus in a subject comprising: (a) introducing papillomavirus or papillomavirus DNA or portions thereof necessary for replication, into an epithelial cell; (b) providing conditions that produce infectious papillomavirus in the epithelial cell, where the conditions comprise the epithelial cell not contacting a fibroblast; and (c) detecting the presence of papillomavirus in the epithelial cell. This method provides a simple method for detecting papillomavirus in a subject by taking the sample, such as a fluid or tissue suspected of containing papillomavirus, and contacting it with an epithelial cell, i.e., a trophoblast, and incubating the same according to the conditions set forth in (10) or in the ATCC information for propagation at 39–40° C. for approximately 9 days to produce papillomavirus in the infected cell, if present in the patient sample. If the sample is a tissue, then the tissue needs to be chopped or ground to solubilize the solid tissue for contact with the cells. The presence of the papillomavirus can be detected by methods known to persons skilled in the art, and includes but is not limited to Hybridcap by Dygene, or another commercially available assay, Virapap. The virions can be prepared from the cell cultures using cesium chloride gradients and detected visually and gradient fractions may be analyzed by Southern blot hybridization to confirm the presence of HPV DNA from the identified bands. Additionally, the presence of papillomavirus DNA, RNA and protein, such as the capsid protein, L1, can be detected using methods as described herein and known to persons skilled in the art. If the presence of papillomavirus is low in the sample, the culturing method of the present invention can be used to amplify the amount of papillomavirus which can be contacting with another trophoblast culture under the culturing conditions and then tested for the presence of papillomavirus by the methods as described.

The present invention further is directed to a method of evaluating the inhibition of a papillomavirus comprising (a) introducing papillomavirus or papillomavirus DNA or portions thereof necessary for replication, into an epithelial cell; (b) providing conditions that produce infectious papillomavirus in the epithelial cell, wherein the conditions comprise the epithelial cell not contacting a fibroblast; (c) contacting a potential inhibitor of papillomavirus with the infectious papillomavirus produced in the epithelial cells; and (d) evaluating the presence or absence of the papillomavirus to determine the effectiveness of potential inhibitors. Additionally, the method may be useful in designing and testing papillomavirus inhibitors.

The present invention also is useful as a method of producing a mutant or recombinant papillomavirus, wherein the method comprises: (a) introducing mutant or recombinant papillomavirus DNA or portions thereof necessary for replication, into an epithelial cell; and (b) providing conditions that produce infectious mutant or recombinant papillomavirus in the epithelial cell, wherein the conditions comprise epithelial cell not contacting a fibroblast. This method is the same method as described above except that that mutant or recombinant DNA or portions thereof is introduced into the epithelial cell. The resulting papillomavirus exhibits the defective, mutant or recombinant phenotype as a result of the mutations and recombined DNA introduced into the target cell. This method provides an opportunity to study the effect of mutations to the papillomavirus genome and is useful for studying the life cycle of papillomavirus. Additionally, recombinant papillomaviruses can be generated using the claimed methods to generate vaccines and for gene therapy purposes. The method of introducing of the papillomavirus DNA is performed by transfecting, lipofecting, or electroporating said papillomavirus DNA into the epithelial cell, as described above, and any other known methods of introducing DNA into eukaryotic cells.

The present invention further is directed to a method of producing a non-keratinocyte epithelial helper cell for production of mutant or recombinant papillomavirus comprising: (a) introducing papillomavirus DNA or portions thereof, into a non-keratinocyte epithelial cell, wherein the DNA or portions thereof, supplements the replication of the mutant or recombinant papillomavirus; and (b) providing conditions that produce said non-keratinocyte epithelial helper cell containing said papillomavirus DNA or portions thereof, that supplements the replication of the mutant or recombinant papillomavirus, wherein the conditions comprise the epithelial cell not contacting a fibroblast. This non-keratinocyte epithelial helper cell produced by this method is useful in propagating mutant or defective HPV that could not replicate without the functions provided by the helper cell.

A method of reducing the risk of spontaneous abortion caused by papillomavirus comprising administering to a subject at risk of spontaneous abortion a drug that inhibits papaillomavirus. The drug can include papillomavirus anti-sense agents, anti-papillomavirus immunotherapy, such as papillomavirus neutralizing antibodies, AAV-dendritic cell containing papillomavirus proteins or papillomavirus protein pulsing therapies as described in U.S. Ser. No. 60/147,263, incorporated in its entirety by reference, antagonists to trophoblast papillomavirus binding sites, and other appropriate drugs and compounds.

Experimental Section

Activity of HPV in Trophoblasts

The finding that HPVs are present in trophoblasts prompted the analysis of HPV type 16 (a common genital HPV) biological activity in this newly identified target cell type. The biological activity of HPV-16 is studied in the 3A(tPA-30-1) (ATCC CRL-1583) trophoblast cell line which has been partially transformed with a temperature sensitive SV40 large T antigen. These cells have an essentially normal, non-transformed phenotype at 40° C. as judged by the synthesis of human chorionic gonadotropin and alkaline phosphatase, and are mortal (10).

An experiment was performed to determine whether HPV-16 would replicate in these cells using the infectious center assay which is intended to identify individual cells with high DNA copy numbers, and was carried out similarly to that described previously. (26) One million 3A cells were transfected with 1 $\mu$g of HPV-16 genomic DNA, cut (Bam HI) from plasmid (pAT-HPV- 16) (11), religated and recircularized via lipofection using FuGENE 6 (Roche Diagnostics Corporations). At the indicated times post-transfection, $10^4$ cells were applied to a nylon membrane and lysed. All of the membranes were then probed with $^{32}$P-HPV-16 DNA. The transfected 3A cells were always grown at 40° C. The results shown in FIG. 1A show positive signals at days 9–24. Particularly, FIG. 1A discloses that the HPV-positive signal and copy number in the 3A cells increases to day 15, becomes somewhat reduced at day 21, and declines thereafter. As can be seen there appears to be a number of high signal spots at day 15. CaSki cells ($1\times10^3$), used as positive controls, contain about 600 copies of HPV-16 (12). The appearance of a limited number of strong individual spots suggests that high level HPV-16 replication is limited to only a subset of the 3A cells.

Figure 1B:
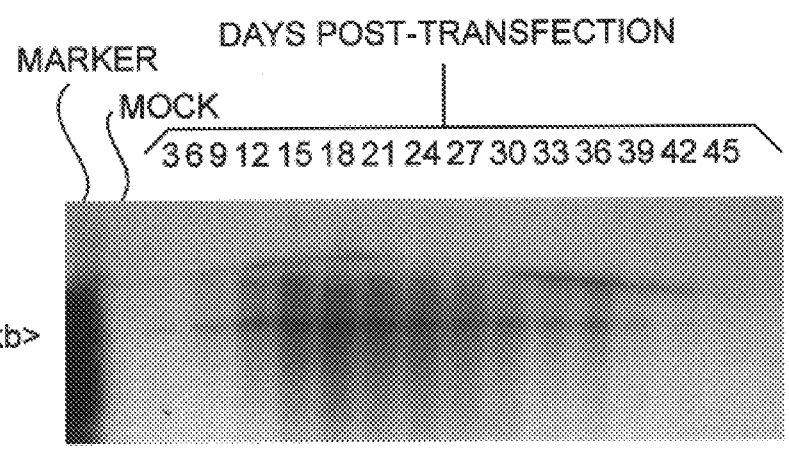

The HPV-16 replication levels were then analyzed in another, more exhaustive, time course experiment by Southern blot, shown in FIG. 1B. Again, 1 μg of HPV-16 reconstituted genomic DNA was transfected into a series of identical 3A cultures ($5 \times 10^5$ cells). Total cellular DNA was harvested at the indicated times, then 15 pg of the total cellular DNA was digested with Dpn I to remove input bacterial DNA, and Bam HI to drive all of the HPV-16 DNA into one band. The DNA was then size separated by agarose gel electrophoresis, Southern blotted and probed with $^{32}$P-HPV-16 DNA. As can be seen in FIG. 1B, a strong 8 kb band is seen in almost all the lanes, suggesting that the DNA HPV-16 DNA is likely present episomally. The replication levels increase until day 12, plateaus until day 21, and then steadily decline afterwards. In the early stages significant DNA levels are not seen until day 9 and increase to the maximum at day 12. It is interesting to note that these are roughly the same time kinetics for HPV replication in the organotypic epithelial raft culture system, the only other tissue culture system known to be fully productive for HPVs. The presence of a strong 8 kb band in these specimens is consistent with episomal HPV-16 genomes or, less likely, head-to-tail integrated concatemers. To more clearly indicate that the majority of the DNA was episomal, the DNA is analyzed without digestion and with multiple zero cut restriction enzymes. Finally, the basic structure of the replicated HPV-16 genome is analyzed with multiple cut restriction enzymes.

Figure 1C:
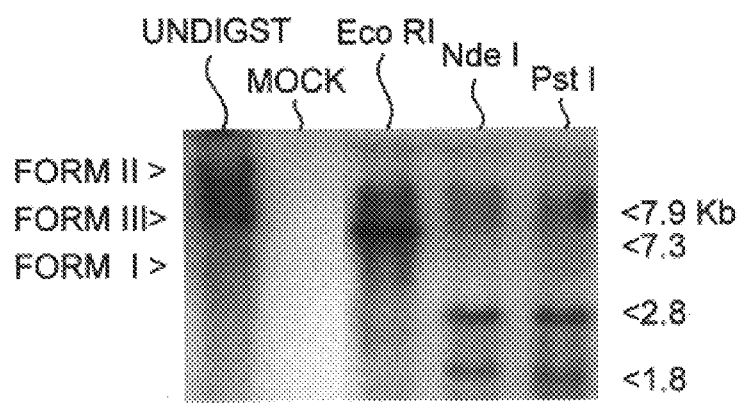

FIG. 1C provides another analysis by Southern blot assay. This experiment is similar to the experiment shown in FIG. 1B, with harvesting at day 14 and digestion with the indicated restriction enzymes. As shown in FIG. 1C, the appearance of forms I, II, and III in undigested DNA, and the appropriate sized bands in the digested lanes indicates that the viral genome is episomal and that no deletions or rearrangements were seen.

HPV MRNA Expression

Figure 2:
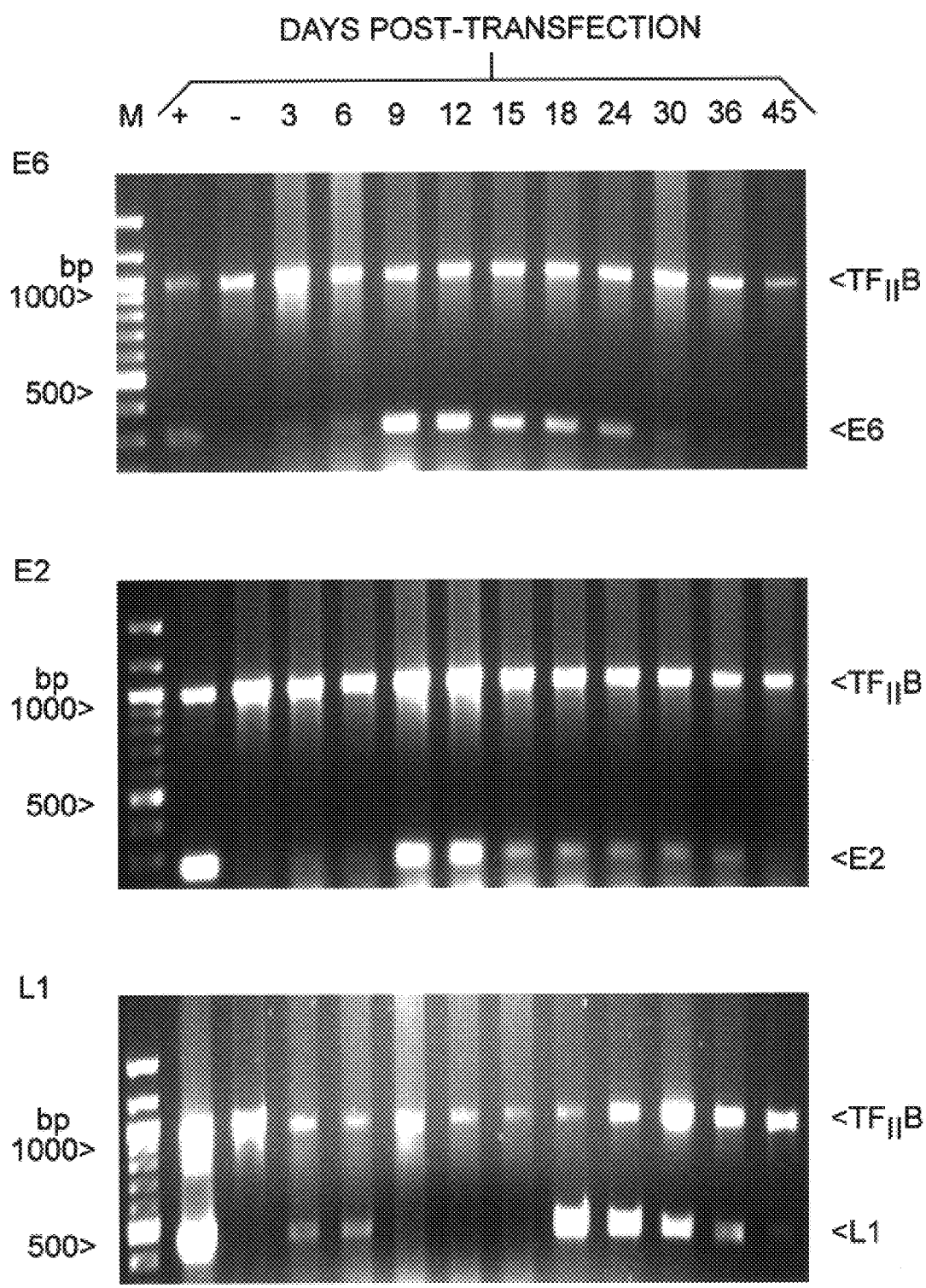
FIG. 2: HPV-16 RNA expression in 3A trophoblasts. A E6 mRNA expression. E6 mRNA was analyzed by reverse transcription-polymerase chain reaction (RT-RCR). As in FIG. 1, 3A cells were lipofected at day 0 and total RNA isolated using TRIZOL reagent (Life Technologies Inc.) according to the manufacturer's protocol, and treated with RNase-free DNase I (Promega Co.) 5U/:g for 4 hours at 37° C. Messenger MRNA was then separated using the Oligotex MRNA Mini Kit (QIAGEN Inc.) according to the supplier's instruction. The first-strand cDNA synthesis was performed at 37° C. for 2 hour in a final volume of 25 ml [2 mg denatured mRNA, 5 ml 5 reaction buffer, 200 U of M-MLV Reverse Transcriptase RNase H Minus (Promega Co.), 5 ml each of the four dNTPs (10 mM each), 0.5 mg oligo (dT)15 (Promega Co.) and 30 U of RNasin (Promega Co.)]. PCR amplification of the cDNA was performed in a 100 ml reaction volume, which contained 2.5U Taq DNA polymerase (Fisher Scientific Co.); 10 mM Tris-HCl, pH 8.3; 50 mM KCl; 2 mM $MgCl_2$; 200: M dNTPs; 1.0:M of each upstream and downstream primer specific for cDNA template and 10:1 cDNA template. The E6 primer set used was —ACCACAGTTATGCACAGAGC-3'(SEQ ID NO:1) and 5-AGGACACAGTGGCTTTTGAC-3'(SEQ ID NO:2) to amplify the sequences from nt 139 to 420. A control RT-PCR analysis of expression of the houskeeping gene TFIIB (28) was also undertaken with the primers 5'-GTGAAGATGGCGTCTACCAG-3'(SEQ ID NO:3) and 5'-GCCTCAATTTATAGCTGTGG-3'(SEQ ID NO:4), which amplified nt 356–1314 of that mRNA. To insure that DNA wasn't contributing to the results a direct PCR was also undertaken. The products were then analyzed on an agarose gel, stained with ethidium bromide, and visualized by ultraviolet light. Note that the expression of TFIIB is relatively stable over the time course while significant E6 RNA expression starts at day 9, declining thereafter. B E2 mRNA expression. E2 mRNA was analyzed by RT-PCR similar to E6, except for using the E2 specific primer set 5'-AACACAGACGACTATCCAGC-3'(SEQ ID NO:5) and 5'-ATGCCATGTAGACGACACTG-3'. (SEQ ID NO:6) to amplify from nt 3454–3696. Note that the expression is like E6, starting at day 9, then declining. C L1 mRNA expression. L1 mRNA was similarly analyzed as E6 and E2, except that the L1 specific primer set 5'-GCACAGGGCCACAATAATGG-3'(SEQ ID NO:7) and 5'-CGTCCTAAAGGAAACTGATC-3'(SEQ ID NO:8) was used to amplify from nt 6583 to 7033. Note that L1 RNA expression is different than E6 or E2, starting at day 18, and then declining. The small blip of early L1 expression was reproducible but much lower than expression at later times.
Figure 3:
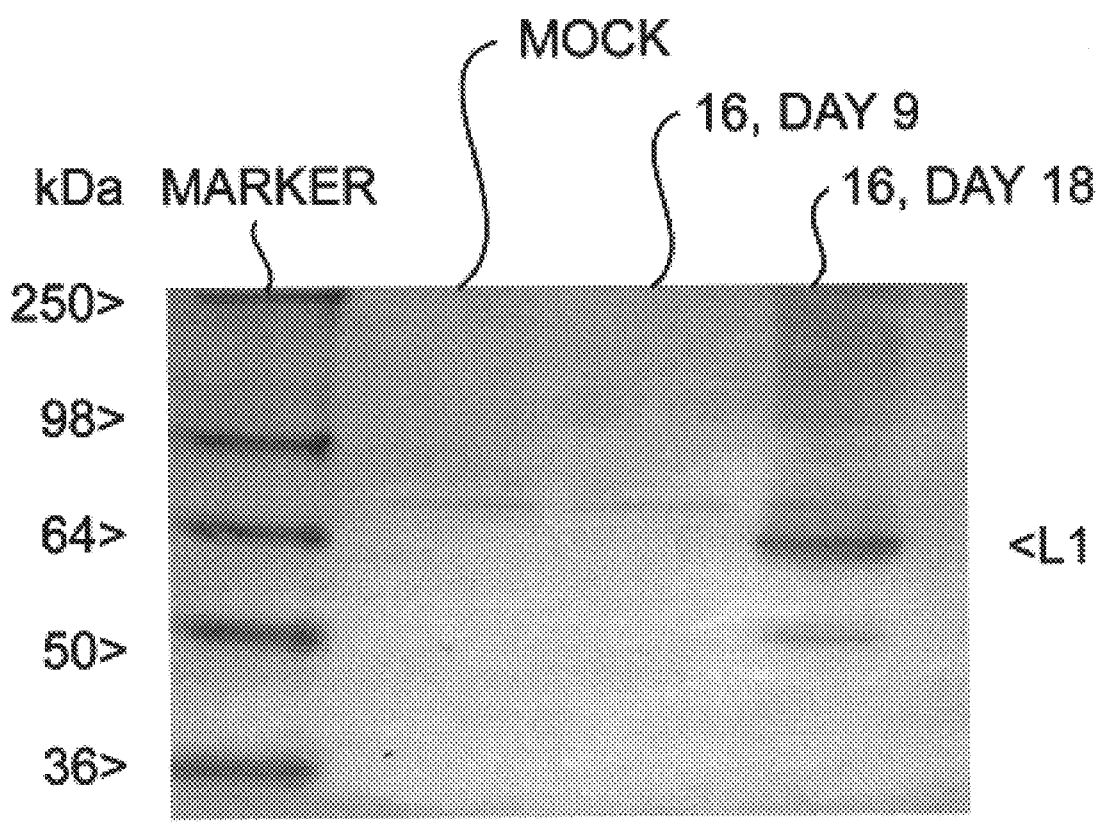
FIG. 3: Production of L1 capsid protein by HPV-16 in trophoblasts. Cells were treated as in FIG. 2 except that total proteins were isolated at days 9 and 18 and analyzed for L1 protein. Western blot was done according to the routine protocol. After the electrophoresis and transfer were finished, the nitrocellulose membrane (Amersham Life Science Co.) was blocked with blocking buffer (The Protein Detector Western Blot Kit, KPL, Inc.) for 1 hour. The purified mouse anti-human HPV-16 L1 monoclonal antibody (CAMVIR-1, mouse IgG2a, PharMingen International) was added to the buffer (1.5 mg/ml). The membrane was incubated at 4° C. overnight, and then washed with washing buffer (The Protein Detector Western Blot Kit) five times. The membrane was put into 1 'blocking buffer containing peroxidase-labeled secondary antibody (Goat anti-mouse IgG) (H+L), 1:1000, the Protein Detector Western Blot Kit) and incubated at room temperature for 1 hour. TMB substrate (The Protein Detector Western Blot Kit) was applied onto the membrane after the membrane was washed 6 times. The reaction was stopped when the suitable color intensity was observed. Note that no L1 was expressed in the untransfected cells or the transfected cells harvested at day 9. In contrast, the cells transfected and harvested at day 18 show a strong band at the size consistent with L1 protein.

Given that HPV-16 was replicating its DNA in the 3A trophoblasts, next, mRNA expression was analyzed by reverse transcriptase/polymerase chain reaction amplification (RT/PCR) using poly-A selected RNA as a template. E6, E2, and L1 targeting primer sets were used to observe the potential of "early" and "late" gene expression. Also included was a primer set for $TF_{II}B$ as an additional constitutive cellular control. After RT/PCR the products were analyzed by agarose gel electrophoresis and ethidium bromide staining. The results for E6 mRNA expression, shown in FIG. 2A, demonstrate that significant E6 expression does not take place until day 9, and then declines. The expression of E2 mRNA was similar (FIG. 2B), and follows that of the HPV-16 DNA replication. Next, the expression of L1 mRNA was analyzed, as shown in FIG. 2C. As can be seen the expression of significant L1 RNA levels do not take place until day 18, 9 days later than E2. Thus, this late gene is expressed late relative to the early genes, as would be expected. The early low level expression of L1 on days 3 and 6 was a reproducible event. As L1 RNA was expressed at day 18, we further analyzed for L1 protein expression by Western blot analysis. Again, 3A cells were transfected with HPV-16 DNA and harvested at days 9 and 18. Total proteins were isolated, separated by SDS-polyacrylamide gel electrophoresed, and transferred to nitrocellulose by standard methodologies. The blot was probed with anti-HPV-16 L1 monoclonal antibody CAMVIR-1 (Amersham Life Science Co.). The results are shown in FIG. 3 and demonstrate that L1 protein is expressed at day 18, but not at day 9, consistent with the RNA findings.

Papillomavirus L1 Expression

Figure 4A:
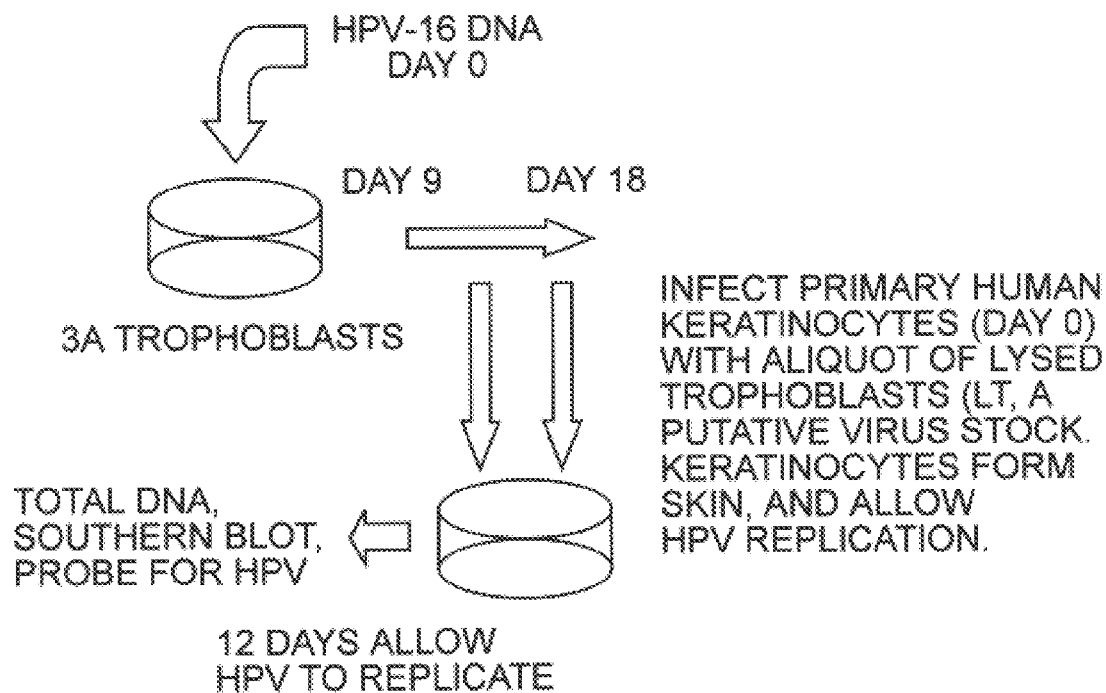
FIG. 4: Production of HPV-16 virions in the trophoblasts. The generation of HPV-16 virions was measured by the ability of trophoblast lysates to infect normal keratinocytes which were then placed into an organotypic raft culture system to generate a stratified squamous epithelium product for HPV. "RILT-16" is an abbreviation for rafts infected with lysed trophoblasts which had been transfected with HPV-16. A The experimental scheme for showing infectious virus production is diagramatically presented. B As in FIGS. 1 and 2. 3A trophoblasts were mock or HPV-16 lipofected, and then at the indicated times the cells were freeze-thawed three times to lyse the cells, filtered, and treated with DNAseI 100 units/ml for 1 hour. The generated putative virus stocks were then used to infect normal keratinocytes 5×10$^6$ cells, for 4 hours. These cells were then trypsinized and seeded onto J2 containing collagen rafts as described by Meyers (1992) to generate an organotypic epithelial raft culture system (15). HPVs are known to productively replicate in this system. Twelve days after raising the raft to the air interface, sufficient time to allow for HPV replication, the raft tissues were harvested, total cellular DNA was isolated, agarose gel electrophoresed, Southern blotted, and probed with 32P-HPV-16 DNA. Note that the mock and day 9 lysate didn't produce any evidence of HPV-16 infection, while the day 18 lysate showed a significant 8 kb HPV-16 specific band.
Figure 4B:
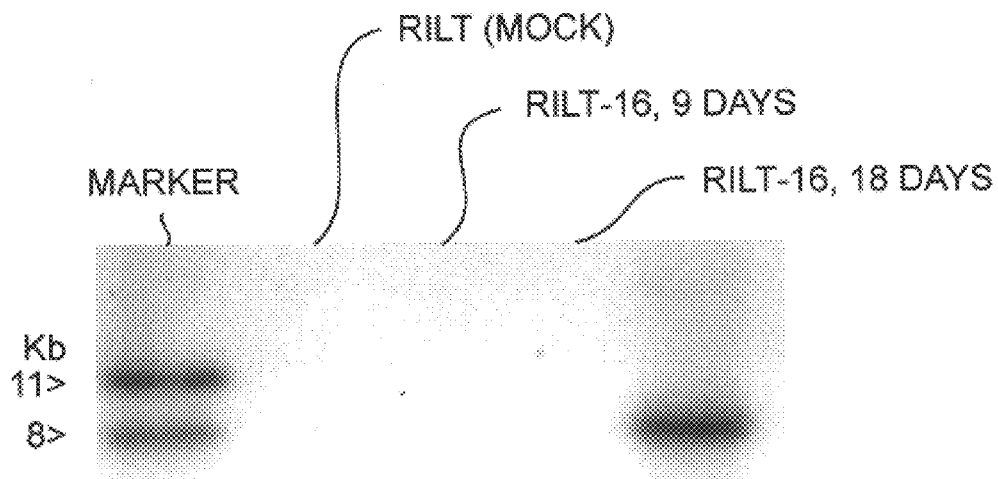

The strong RNA and protein expression of L1 on day 18 suggested the possibility that HPV-16 progeny virions were likely being produced. Production of the L1 protein leads to self assembly of pseudo-particles even in the absence of DNA (13,14). To analyze if HPV-16 virions were being produced, putative virus stocks were generated from HPV-16-transfected trophoblast cultures at day 9 (no L1) and day 18 (L1). The trophoblasts were frozen-thawed, filtered, treated with 100 units/ml DNAse I for one hour and then used to infect normal primary human foreskin keratinocytes. The keratinocytes were then seeded onto collagen rafts containing J2 fibroblasts and then raised to the air to stimulate the formation of a stratified squamous epithelium which would be favorable for productive papillomavirus replication (organotypic raft culture system)(15). The experiment is schematically described in FIG. 4A. Any HPV-16 virions produced in the trophoblasts would infect the keratinocytes and be amplified in the raft "skin" by day 12. At that time total raft DNA isolated and analyzed for HPV-16 sequences. The results, shown in FIG. 4B, indicate no evidence of HPV-16 replication from the day 9 lysate (RILT, rafts infected with lysed trophoblasts), while the rafts infected with the day 18 lysates show a strong 8 kb band upon Bam HI digestion. These day are consistent with HPV-16 virion production on day 18.

Neutralizing Antibody Effect on HPV-16

Figure 5:
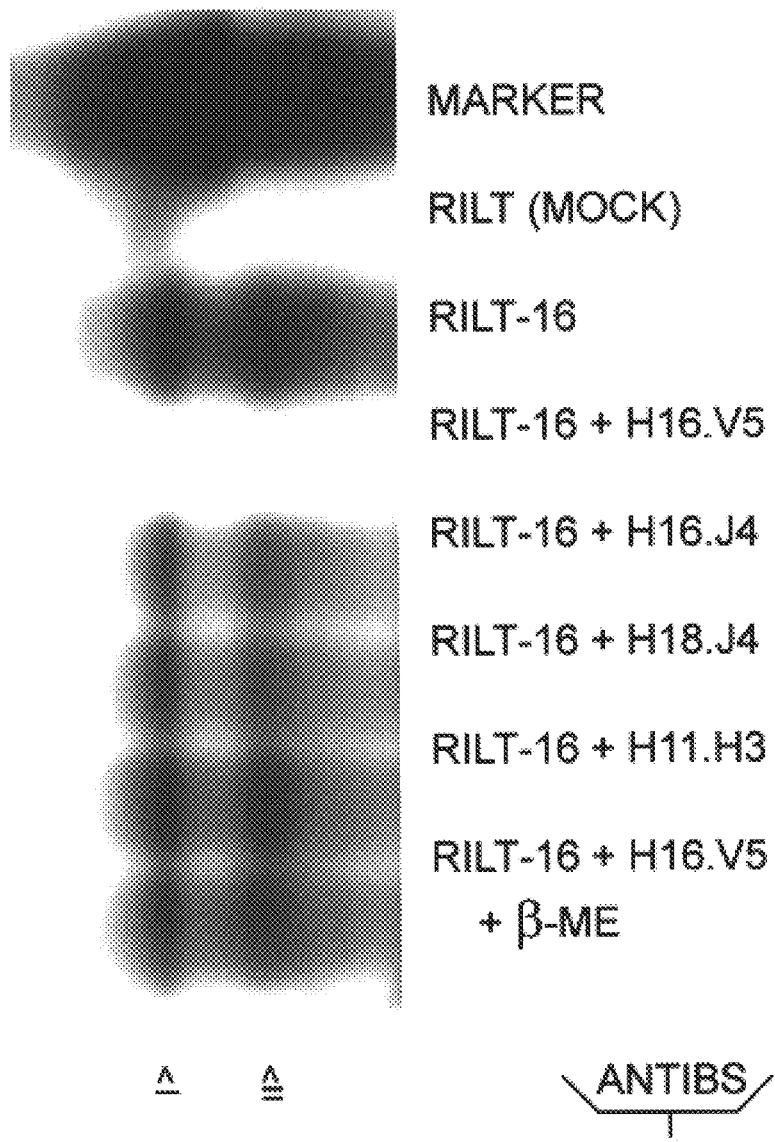
FIG. 5: Specific antibody neutralization of HPV-16 virions produced in trophoblasts. This experiment was similar to FIG. 3 except that the HPV-16 virus stocks were pretreated with the indicated antibodies before infecting the keratinocytes. In addition, H16.V5 was also treated with β-ME. Note that only untreated H16. V5, known to neutralize HPV-16, was able to prevent the infection of the raft tissue. These data are fully consistent with HPV-16 replication and virion production at day 18.

To further support that HPV-16 generated infectious virions in trophoblasts, an antibody neutralization experiment was undertaken using a series well characterized antibodies. The HPV-16 virus stocks/lysed trophoblasts were mixed with H16.V5(HPV-16 neutralizing antibody); H16.J4 (HPV-16 non-neutralizing antibody); HPV-18. J4 (HPV-18 neutralizing antibody) and H 1.H3 (PV-1 1 neutralizing antibody) respectively (1:1000)(16,17). Finally, H16.V5 was also treated with 0.2 M β-mercaptoethanol (β-ME) at room temperature for 30 minutes, it was also mixed with the HPV-16 virus stock. All of the mixtures were incubated at 37° C. for 1 hour, and then added to the culture dishes containing the keratinocytes. After 4 hours incubation, the keratinocytes were transferred onto top of collagen matrixes and the experiment proceeded as in FIG. 3. The results (FIG. 5) show that only the antibody, H16.V5, known to neutralize HPV-16 had a consistent effect on the HPV-16 virus stock/trophoblast lysate, while all other antibodies did not. Furthermore, treatment of H16.V5 with β-ME knocked out this neutralization.

A method for producing trophoblast HPV helper cell lines for the production of mutant or recombinant HPV virus. HPV genes, as DNA fragments, are introduced into trophoblasts to generate helper cell lines for HPV production. These cell lines can be generated by a variety of methods such as G418 [Neo] selection as described herein: Five μg of the HPV-16 DNA containing plasmid will be cotransfected along with 1 μg of pSV2-Neo using TFX50 (Promega, used as directed by the manufacturer) into 6 cm plates of 3A trophoblasts. Similar experiments may also be undertaken using immortalized trophoblast cell lines, such as JAR and BeWo. Two days after transfection, the cells will be selected with 400 μgs of G418, for two weeks. These resulting cells provide the corresponding missing gene functions which have been deleted in the mutant or recombinant HPV virus. The mutant HPV can be introduced by DNA transfection or virus infection. Virus production proceeds as shown in FIG. 1 and as described in the description of the experiments depicted therein.

The cited publications are herein incorporated in their entirety by reference.

REFERENCES

1) Hermonat, P. L., Han, L., Wendel, P., Quirk, J. G., Stern, S., Lowery, C., and Rechtin, T. L. (1997) Human papillomavirus DNA is more prevalent in first trimester spontaneously aborted products of conception compared to elective specimens. Virus Genes 14:13–17.
2) Hermonat, P. L., Kechelava, S., Lowery, C. L., and Korourian, S. (1998) Trophoblasts are the preferential target for human papillomavirus infection in spontaneously aborted products of conception. Human Pathology 29:170–174.
3) Malhomme, O., Dutheil, N., Rabreau, M., Armbruster-Moraes, E., Schlehofer, J. R., and Dupressoir, T. (1997) Human genital tissues containing DNA of adeno-associated virus lack DNA sequences of the helper viruses adenovirus, herpes simplex virus or cytomegalovirus but frequently contain human papillomavirus DNA. [Journal Article] Journal of General Virology. 78 (Pt 8):1957–62.
4) Manavi, M., Czerwenka, K. F., Schurz, B., Knogler, W., Kubista, E., and Reinold, E. (1992) [Latent cervical virus infection as a possible cause of early abortion]. [German] [Journal Article] Gynakologisch-Geburtshilfliche Rundschau. 32(2):84–7.
5) Rabreau, M., and Saurel, J. (1997) [Presence of human papilloma viruses in the deciduousmembranes of early abortion products (letter)]. Presse Medicale. 26(36):1724.
6) Sikstrom, B., Hellberg, D., Nilsson, S., Brihmer, C., and Mardh, P. A. (1995) Contraceptive use and reproductive history in women with cervical humanpapillomavirus infection. Advances in Contraception. 11(4):273–84.
7) Pao, Q., Hor, J. J., Wu, C. J., Shi, Y. F., Xie, X., and Lu, S. M. (1995) Human papillomavirus DNA in gestational trophoblastic tissues and choriocarcinoma. International J. Cancer 63:505–509.
8) Armbruster-Moraes, E., Ishimoto, I. M., Leao, E., and Zugaib, M. (1994) Presence of human papillomavirus DNA in amniotic fluids of pregnant women with cervical lesions. Gyn. Oncol. 54:152–158.
9) Clark, D. A., Banwatt, D., Croy, B. A. (1993) Murine trophoblast failure and spontaneous abortion. Amer. J. Reprod. Imm. 29:199–205.
10) Chou, J. Y. Human placental cells transformed by tsA mutants of simian virus 40: a model system for the study of placental functions. Proceedings of the National Academy of Sciences of the United States of America. 75(3):1409–13, 1978
11) Bubb, V., McCance, D. J., and Schlegel, R. DNA sequence of the HPV-16 E5 ORF and the structural conservation of its encoded protein. Virology. 163(1):243–6, 1988
12) Baker, C. C., Phelps, W. C., Lindgren, V., Braun, M. J., Gonda, M. A., and Howley, P. M. Structural and transcriptional analysis of human papillomavirus type 16 sequences in cervical carcinoma cell lines. Journal of Virology. 61(4):962–71, 1987
13) Kirnbauer, R., Booy, F., Cheng, N., Lowy, D. R., and Schiller, J. T. Papillomavirus L1 major capsid protein self-assembles into virus-like particles that are highly immunogenic. Proc. Natl. Acad. Sci. USA 89(24):12180–4, 1992
14) Kirnbauer R. Booy F. Cheng N. Lowy D R. Schiller J. T. Papillomavirus L1 major capsid protein self-assembles into virus-like particles that are highly immunogenic. Proc. Natl. Acad. Sci. USA 89(24):12180–4, 1992
15) Craig Meyers (1996) Organotypic (raft) epithelial tissue culture system for the differentiation-dependent replication of papillomavirus. Methods in Science 18:201–210
16) Roden R. B. Armstrong A. Haderer P. Christensen N. D. Hubbert N. L. Lowy D. R. Schiller J. T. Kirnbauer R. Characterization of a human papillomavirus type 16 variant-dependent neutralizing epitope. Journal of Virology. 71(8):6247–52, 1997
17) Christensen N. D. Reed C. A. Cladel N. M. Hall K. Leiserowitz G. S. Monoclonal antibodies to HPV-6 L1 virus-like particles identify conformational and linear neutralizing epitopes on HPV-11 in addition to type-specific epitopes on HPV-6. [Journal Article] Virology. 224(2):477–86, 1996
18). Melbye M. Frisch M. The role of human papillomaviruses in anogenital cancers. Seminars in Cancer Biology. 8(4):307–13, 1998
19) Neuqebauer, R., Kline, J., Stein, Z., Shout, P., Warburton, D., and Susser, M. (1996) Association of stressful life events chromosomally normal spontaneous abortion. Am. J. Epidem. 143:588–596.
20) Kline, J., Levine, B., Kinney, A., Stein Z., Susser, M., and Wurburton, D. (1995) Cigarette smoking and spontaneous abortion of know karyotype. Prices data but uncertain inferences. Am. J. Epidem. 141:417–427.
21) Coste, J., Job-Spira, N., Fernandez, H. (1991) Risk factors for spontaneous abortion: a case control study in France. Hum. Repro. 6: 1332–1337.
22) Dominguez, V., Calle, E., Ortega, P., Atasio, P., Valero de Bernabe, J., and Rey Calero, J. (1991) Adjusting risk factors in spontaneous abortion by multiple logistic regression. Europ. J. Epidem. 7:171–174.
23) Tan, N. H., Yahya, A., and Adeeb, N. (1995) Sociobiological risk factors for spontaneous abortionin Malaysia. J. Ostet. Gyn. 21:313–318
24) Cordier, S., Deplan, F., Mandereau, L., Hemon, D. (1991) Paternal exposure to mercury and spontaneous abortions. Brit. J. Indust. Med. 48:375–381.
25) Stucker, I., Caillard, J. F., Collin, R., Gout, M., Poyen, D., and Hemon, D. (1990) Risk of spontaneous abortion amoung nurses handling antineoplastic drugs. Scand. J. Work, Environ. Health 16:102–107.
26) Parazzini, F., Bocciolone, L., Fedele, L., Negri, E., La Vecchia, C., and Acaia, B. (1991) Risk factors for spontaneous abortion. Internat. J. Epidem. 20:157–161.
27) Barrington, J. W., Lindsay, P., James, D., Smith, S., and Roberts, A. (1996) Selenium deficiency and miscarriage: a possible link? Brit. J. Obstet. Gyn. 103:130–132.
28) Risch, H. A., Weiss, N. S., Clarke, E. A., Miller, A. B. (1988) Risk factors for spontaneous abortion and its recurrence. Am. J. Epidem. 128:420–430.
29) Schlehofer, J. R., Gissmann, L., Matz, B. and Hausen, H. Z. (1983) Herpes simplex virus-induced amplification of SV40 sequence in transformed Chinese hamster embryo cells. Int. J. Cancer 32, 99–103.
30) Ha, L., Lane, W. S. and Reinberg, D. (1991) Cloning of a human gene encoding the general transcription initiation factor IIB. Nature 352, 689–694

We claim:

1. A method of producing infectious papillomavirus in vitro, wherein said method comprises:
   (a) introducing papillomavirus or papillomavirus DNA into a placental cell; and
   (b) providing conditions sufficient for the production of said papillomavirus in said placental cell.

2. The method of claim 1, wherein said placental cell is selected from the group consisting of a trophoblast, a cytotrophoblast, a syncytiotrohoblast, a hyperplastic or displastic trophoblast and a choriocarcinoma.

3. The method of claim 1, wherein said introducing of said papillomavirus or said papillomavirus DNA into said placental cell is performed by one of the methods selected from the group consisting of transfecting into, lipofecting into, electroporating into and contacting with said papillomavirus or papillomavirus DNA.

4. The method of claim 1, wherein said papillomavirus DNA is papillomavirus genomic DNA.

5. The method of claim 1, wherein said papillomavirus DNA is mutant DNA, and when expressed in said placental cell, results in an attenuated or defective papillomavirus.

6. The method of claim 1, wherein said papillomavirus is a human papillomavirus.

7. The method of claim 1, further comprising (c) detecting the presence of papillomavirus.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: primer

<400> SEQUENCE: 1
accacagtta tgcacagagc                                           20

<210> SEQ ID NO 2
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: primer

<400> SEQUENCE: 2
aggacacagt ggcttttgac                                           20

<210> SEQ ID NO 3
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: primer

<400> SEQUENCE: 3
gtgaagatgg cgtctaccag                                           20

<210> SEQ ID NO 4
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: primer

<400> SEQUENCE: 4
gcctcaattt atagctgtgg                                           20

<210> SEQ ID NO 5
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: primer

<400> SEQUENCE: 5
aacacagacg actatccagc                                           20

<210> SEQ ID NO 6
<211> LENGTH: 20
<212> TYPE: DNA
<213> ORGANISM: Artificial Sequence -continued

```
<220> FEATURE:
<221> NAME/KEY: misc_feature
<222> LOCATION: ()..()
<223> OTHER INFORMATION: primer

<400> SEQUENCE: 6
atgccatgta gacgacactg                                                    20

<210> SEQ ID NO 7
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: primer

<400> SEQUENCE: 7
gcacagggcc acaataatgg                                                    20

<210> SEQ ID NO 8
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: primer

<400> SEQUENCE: 8
cgtcctaaag gaaactgatc                                                    20
```